United States Patent [19]

Castaneda et al.

[11] Patent Number: 5,417,669
[45] Date of Patent: May 23, 1995

[54] CATHETER EXCHANGE METHOD AND APPARATUS

[75] Inventors: Javier E. Castaneda, Miami; Caron S. D'Ambruso, Weston, both of Fla.

[73] Assignee: Cordis Corporation, Miami Lakes, Fla.

[21] Appl. No.: 190,384

[22] Filed: Feb. 1, 1994

[51] Int. Cl.⁶ ............................................. A61B 5/00
[52] U.S. Cl. .................................................... 604/264
[58] Field of Search ............... 604/280, 264, 160–161, 604/43, 52, 53, 96, 101, 281, 283; 128/656–658, 637, 772; 606/191–194

[56] References Cited

U.S. PATENT DOCUMENTS

| | | | |
|---|---|---|---|
| 4,747,833 | 5/1988 | Kousai et al. | 604/280 |
| 4,771,777 | 9/1988 | Horzewski et al. | |
| 4,947,864 | 8/1990 | Shockey et al. | |
| 4,983,168 | 1/1991 | Mooreheal | 604/280 |
| 5,135,535 | 8/1992 | Kramer | |
| 5,154,725 | 10/1992 | Leopold | |
| 5,171,222 | 12/1992 | Euteneuer et al. | |
| 5,195,978 | 3/1993 | Schiffer | 604/280 |
| 5,234,407 | 8/1993 | Teirstein et al. | |

FOREIGN PATENT DOCUMENTS

| | | |
|---|---|---|
| 0282143 | 1/1988 | European Pat. Off. |
| 0397357 | 4/1990 | European Pat. Off. |
| WO92/20397 | 11/1992 | WIPO |

OTHER PUBLICATIONS

A document entitled Instructions For Use Marathon Relay (TM) Guiding Catheter Flushing Device (1 Page).
A document entitled Marathon Relay (TM) Guiding Catheters (3 pages).

Primary Examiner—C. Fred Rosenbaum
Assistant Examiner—Manuel Mendez
Attorney, Agent, or Firm—Gerstman, Ellis & McMillin, Ltd.

[57] ABSTRACT

A first catheter surrounds a guidewire, with the first catheter and guidewire each having a distal portion emplaced in the cardiovascular system of a patient. By this invention, the first catheter may be removed without displacing the guidewire. To accomplish this, one may advance an exchange catheter into the patient to a desired position. The exchange catheter surrounds the guidewire and, in turn, is surrounded by the first catheter. One causes a proximal end portion of the guidewire to project outwardly through a longitudinal slit of the exchange catheter, so that the proximal end of the guidewire may be grasped. By this means the guidewire may be retained in the desired position as the exchange catheter is advanced into its position within the first catheter and surrounding the guidewire. One then withdraws the first catheter from the patient, while causing the exchange catheter to be held relatively stationary. Thus the guidewire within the exchange catheter is also retained in relatively stationary position without the need for retention of the guidewire by manual grasping.

19 Claims, 1 Drawing Sheet

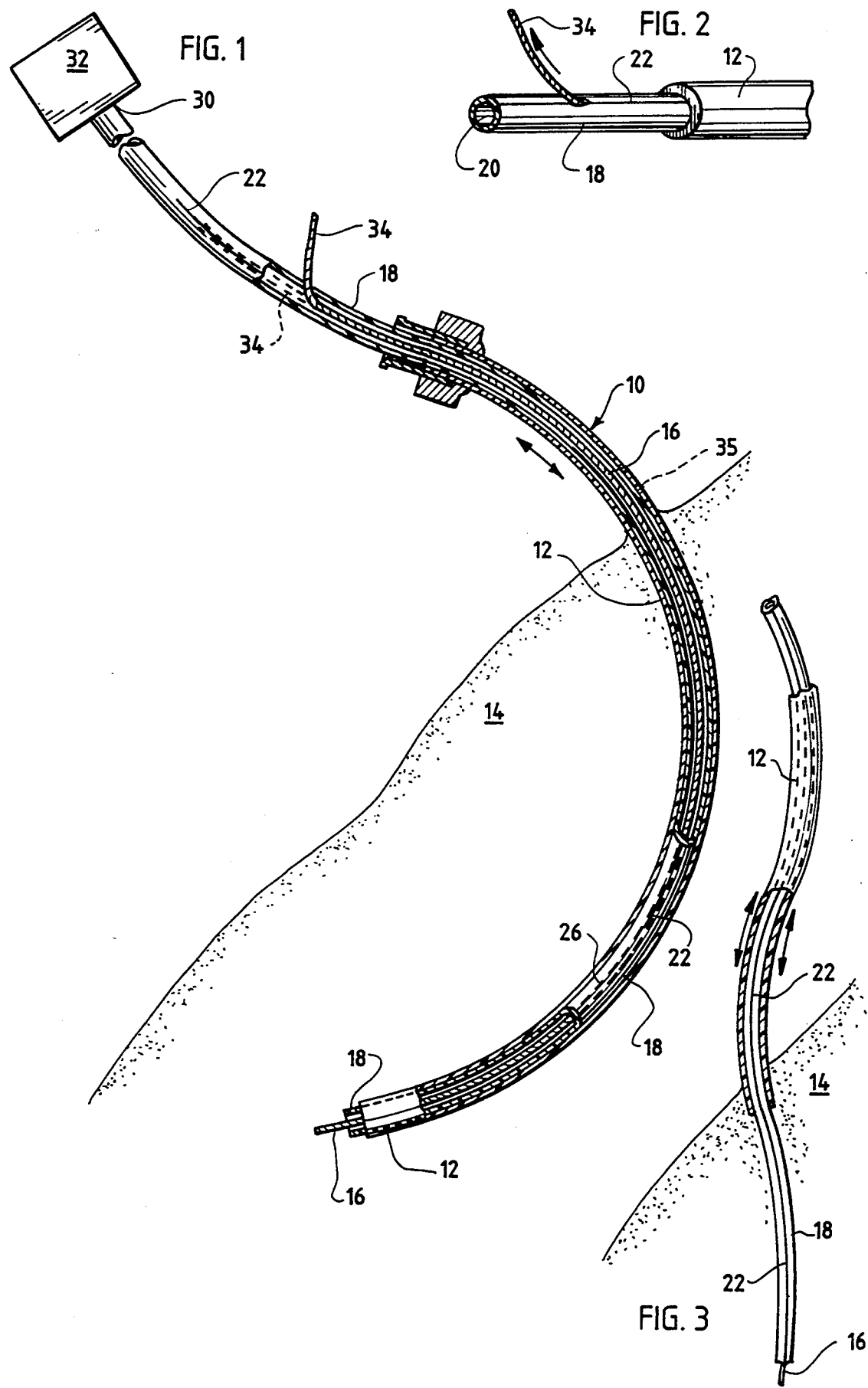

CATHETER EXCHANGE METHOD AND APPARATUS

BACKGROUND OF THE INVENTION

In the field of angiography and angioplasty, it is common for a relatively thick guidewire (e.g. 0.035 inch) to be initially inserted through the cardiovascular system of a patient to the area of a stenosis in a coronary artery. Following this, a guiding catheter may be advanced along the guidewire to a position in the arterial system, typically the aortic root, following which the guidewire may be withdrawn, and replaced with a thinner guidewire (e.g. 0.010–0.018 in.), which is then advanced across the stenosis.

After this has been accomplished, an angioplasty catheter, for example, may be advanced through the guiding catheter and along the thin guidewire which traverses the stenosis, with the hope and expectation that the angioplasty catheter also can pass through the stenosis, to bring a balloon into position for the angioplasty procedure (PTCA).

All things being equal, the cardiologist typically prefers a smaller guiding catheter French size, which requires a smaller access site and PTCA introducer sheath, which carries with it less risk of hematoma. However, the particular interventional situation may turn out to require a larger guiding catheter, after the cardiologist has emplaced the narrower PTCA guidewire, for example so that a stent, a Rotoblader unit, a perfusion balloon, or other technology may be inserted. This may have to be done on an emergency basis, requiring immediate withdrawal of the guiding catheter and introducer and replacement with a larger guiding catheter and introducer.

It has been found, in this circumstance, that it may not be possible to withdraw the guiding catheter without pulling the thin PTCA guidewire with it. Thus, the position of the guidewire traversing the stenosis may be lost, and this loss may be permanent and irretrievable in unfavorable situations.

Additionally, a stiffer guiding catheter or different curve style may be needed to facilitate passage of the guidewire and or balloon through the stenosis and intricate portions of the arterial system. Here also, a replacement of the guiding catheter may be required, and as before, the PTCA guidewire may be dragged back with the withdrawing guiding catheter, so that the cardiologist loses a position of guidewire advancement that he worked so hard to achieve.

In accordance with this invention, a catheter exchange method is provided in which the advancement position of even a very thin and flexible guidewire may be preserved, while a catheter surrounding the guidewire is exchanged, such as a guiding catheter.

There is a body of prior art pertaining to "rapid exchange" catheters, which typically have an aperture in their sides such as a hole or a slit, thus permitting exchange of the balloon without the use of a guidewire extension attached to the proximal end of the guidewire. However, these prior art catheters and techniques fail to solve all of the problems addressed by this invention. Particularly, with respect to a very thin or very flexible guidewire, the above are not used effectively to inhibit the withdrawal of the distal end of the guidewire along with a withdrawing guiding catheter, even if the proximal end of the guidewire is being held in place.

By this invention, better protection against withdrawal of the distal end of a guidewire is provided upon guiding catheter withdrawal. Also, by this invention it becomes possible to withdraw guiding catheters and introducers from a patient without the need for a guidewire extension attached to the proximal end of the guidewire by the use of a new, added exchange catheter, to provide a new form of "rapid exchange" of guiding catheters, both guiding catheters and introducers. Additionally, the same exchange catheter can provide stiffening support to the guidewire to facilitate its advancement through a difficult stenosis or the like.

DESCRIPTION OF THE INVENTION

In this invention, a method is provided for removing from a patient a first catheter which surrounds a guidewire. The first catheter and guidewire each have a distal portion emplaced in the cardiovascular system of a patient. The first catheter can be removed without displacing the guidewire out of a desired position.

In accordance with this invention, one advances into the patient to a desired position an exchange catheter. The exchange catheter surrounds the guidewire and, in turn, is surrounded by the first catheter. During this advancement process, one causes a proximal end portion of the guidewire to project outwardly through a slit of the exchange catheter, for grasping of the guidewire proximal end portion either manually or by some other means. This causes retention of the guidewire in a desired position as the exchange catheter is advanced, with the guidewire sliding along the slit.

One then withdraws the first catheter from the patient, while causing the exchange catheter to remain in relatively stationary position. Thus, the guidewire within the exchange catheter is also retained in relatively stationary position, without the need for retention of the guidewire by manual grasping.

Typically, the first catheter is a guiding catheter which needs to be replaced with another guiding catheter. Additionally, there may be a need to exchange the introducer to accommodate a larger diameter guiding catheter. However, there is no significant limitation on the types of catheters which may be exchanged in accordance with this invention.

Preferably, the side aperture means of the exchange catheter used in this invention is a longitudinal slit which communicates between a catheter lumen and the exterior.

The exchange catheter is also preferably of a length permitting grasping of the proximal end of the exchange catheter as the first catheter, which surrounds the exchange catheter, is fully withdrawn from the patient. Thus, the exchange catheter may act in a manner similar to a guidewire extension, as well as providing its other advantages as described above, permitting a first catheter to be withdrawn without the need for a guidewire extension. One can simply grasp the proximal end of the exchange catheter until the first catheter is fully withdrawn from the patient. Then one can grasp a position on the exchange catheter which is distal to the withdrawn first catheter, to remove the first catheter off of the exchange catheter and to replace it with another catheter surrounding the exchange catheter, for emplacement into the patient.

Also, it is preferred for the exchange catheter to be advanced along the guidewire in guidewire-surrounding relation to a position in which the exchange catheter surrounds at least about three-quarters of the length of the guidewire. It is generally preferable for the exchange catheter to surround as much of the guidewire as possible, prior to withdrawing of the first catheter.

Prior to withdrawing of the first catheter, the proximal end portion of the guidewire is typically placed inwardly through the exchange catheter slit, to be surrounded thereby. Thus, as the first catheter is withdrawn, typically the entire proximal portion of the guidewire, and almost all of its length, will be enclosed by the exchange catheter, so that the guidewire will not be subjected to frictional forces created by the withdrawing of the first catheter. Thus, the guidewire will be retained in its desired position as the first catheter is withdrawn.

Typically, the longitudinal slit of the exchange catheter is spaced from the catheter ends, with the slit communicating through the catheter between the lumen and the catheter exterior.

After withdrawing of the first guiding catheter and/or introducer, a second guiding catheter and/or introducer catheter is commonly threaded over the proximal end of the exchange catheter and advanced distally along the exchange catheter into the patient to a desired position. This also may be accomplished without changing the position of the exchange catheter or the guidewire, by grasping the exchange catheter first at a point distal to the second catheter and then at its proximal end when permitted by second catheter advancement. During or after implantation of the second catheter, the guidewire proximal end portion may be caused to project again out of the slit, to be grasped. Then, the exchange catheter may be withdrawn from the patient. This is preferably accomplished, so as not to significantly disturb the position of the guidewire, by withdrawing the exchange catheter in short steps of motion, on the order of an inch or two. Between such steps of motion, the proximal end portion of the guidewire in the slit may, as necessary, be manually advanced relative to the exchange catheter by an amount corresponding to each step of motion, to keep the guidewire in its substantially desired position as the exchange catheter is withdrawn.

Thus, by the above method a guiding catheter may be replaced without dislodging a PTCA guidewire out of desired position. Up to the present time that has frequently been an interventional nuisance. Additionally, as desired, introducers or other catheters may also be exchanged so that the cardiologist can use a larger sheath to accommodate larger diameter catheters, with similar beneficial results. Also, the exchange catheter may provide stiffness to the guidewire which facilitates its advance through difficult arterial sites, and possibly even through the stenosis itself.

Preferably, for convenience the exchange catheter may be unrolled from a spool or hoop as the exchange catheter is advanced into the patient. This provides a significant advantage over a guidewire extension, for example, by providing compact storage of the exchange catheter until it is in use. The exchange catheter may be rerolled with the spool or hoop between catheter exchanges for convenient storage.

DESCRIPTION OF THE DRAWINGS

Referring to the drawings, FIG. 1 is an elevational view, taken partially in longitudinal section, of the catheter system of this invention, shown implanted in the vascular system of a patient, and permitting removal and replacement of a guiding catheter as part of the system;

FIG. 2 is a fragmentary, perspective view of a detail of the catheter system of FIG. 1; and FIG. 3 is an elevational view, taken partly in section, of the catheter system of FIG. 1 showing the outer guiding catheter being either removed or replaced.

DESCRIPTION OF SPECIFIC EMBODIMENTS

Referring to the drawings, FIG. 1 shows a catheter system 10 which comprises a first catheter 12, specifically a guiding catheter of conventional design for angioplasty procedures, implanted in a patient 14 about a guidewire 16, which also may be of conventional design.

A flexible exchange catheter 18 defines a catheter lumen 20 extending through the proximal and distal ends of exchange catheter 18. Exchange catheter 18 also defines a slit 22 which communicates between lumen 22 and the exterior of the exchange catheter. In this embodiment, slit 22 is spaced from the ends of exchange catheter 18.

Exchange catheter 18 also defines a distal catheter tip 24 which may be made of a relatively soft polymer material, when compared with the material of the balance of the catheter. The major, proximal portion 26 of exchange catheter 18 may be made of nylon having a shore D Durometer of 60–80. Such a level of stiffness provides a catheter that remains flexible, but which supports guidewire 16 to facilitate its advancement as necessary through the arterial system of a patient.

It can be seen from the drawings that exchange catheter 18 is substantially coaxially positioned in a relation which is surrounding the great majority of guidewire 16. Catheter 18, in turn, is surrounded by the first, guiding catheter 12 along a substantial portion of the length of guidewire 16 and exchange catheter 18.

Preferably, exchange catheter 18 is more than twice the length of first catheter 12. This permits the easy removal of first catheter 12 from the configuration of FIG. 1, in a manner as illustrated by FIG. 3. The proximal end 30 of exchange catheter 18 may be manually grasped as guiding catheter 12 is pulled outwardly from the patient, to retain both exchange catheter 18 and guidewire 16 in their desired positions. Reel 32, upon which exchange catheter 18 may be initially wound prior to use, may be removed to facilitate removal of guiding catheter 12 from its surrounding relationship with exchange catheter 18 and guidewire 16.

If desired, guiding catheter 12 which is removed and replaced may be of any other desired catheter type such as a balloon catheter for angioplasty. Additionally, catheter 12 may be a catheter sheath introducer, which is similarly replaced in accordance with this invention.

Specifically, the replacement of catheter 12 with a new catheter may be accomplished in accordance with this invention as follows:

In an initial configuration, first catheter 12 is positioned as shown in FIG. 1, surrounding guidewire 16 which is also positioned as shown, without exchange catheter 18.

At some point of the medical procedure, the physician determines that a new guiding catheter is needed: perhaps a guiding catheter which is stiffer, or of larger diameter or different shape, to accommodate an instrument that is larger than a typical PTCA catheter. In the prior art situation there would be little choice in such a circumstance but to withdraw guiding catheter 12, which would in all likelihood result in the corresponding withdrawal of guidewire 16, particularly when the guidewire is an ultra thin, flexible PTCA guidewire. By so doing, the valuable advancement position of the guidewire may be lost, and in some circumstances may never again be achievable, as when crossing of the stenosis has been achieved, but a stenosis spasm takes place, preventing reinstallation of the guidewire crossing the stenosis.

In accordance with this invention, one advances into the patient an exchange catheter 18 which, as shown, surrounds guidewire 16 and in turn is surrounded by first catheter 12. One advances catheter 18 while causing a proximal end portion 34 of guidewire 16 to project outwardly through slit 22 of the exchange catheter 18 as shown in FIGS. 1 and 2. One can grasp guidewire end 34 to retain the guidewire in its desired position as exchange catheter 18 is advanced, with guidewire end 34 sliding in relatively proximal direction along the slit 22 of catheter 18.

Then, when a position substantially similar to that of FIG. 1 is achieved, it is possible to withdraw first catheter 12 from the patient, while causing exchange catheter 18 to be relatively stationary. This can be accomplished by holding proximal end 30 of the exchange catheter, while preferably tucking the end 34 of guidewire 16 through slit 22 into the lumen 20 of catheter 18, as shown in dotted lines in FIG. 1. Thus, at least the great majority of guidewire 16 is protected from sliding friction exerted by catheter 12 as it is being withdrawn outwardly from the patient (FIG. 3), since guidewire 16 is separated from catheter 12 by exchange catheter 18.

Accordingly, one can hold the distal end of exchange catheter 18 and prevent both guidewire 16 and exchange catheter 18 from being proximally dislodged as catheter 12 is drawn outwardly in the proximal direction. As said before, if catheter 18 is long enough, the entire guiding catheter can be easily removed in a conventional manner while one can manually retain a hold on exchange catheter 18, first at proximal end 30, and finally at a portion 35 of catheter 18 immediately outside of the entry point into the patient, while catheter 12 is removed off the proximal end 30 of catheter 18. All this is accomplished without disturbing guidewire 16.

Following this, after the first catheter 12 has been withdrawn, a second catheter, typically another guiding catheter, is threaded over the proximal end 30 of exchange catheter 18 and advanced distally along the exchange catheter, into the patient to a desired position. This relationship of the second catheter is also illustrated by FIGS. 1 and 3, with the second guiding catheter being represented by the catheter of reference number 12.

The advancement of the new guiding catheter 12 is about as easily facilitated as the withdrawal of the old guiding catheter, by performing the process in reverse.

Exchange catheter 18 may be unrolled off of spool 32, which may be of a conventional design, to reduce the cumbersome handling of the exchange catheter. Catheter 18 may be quite long as described above, but may be less inconvenient to handle because of the use of spool 32.

After this, exchange catheter 18 may be withdrawn from the patient. This may be accomplished by pulling proximal end 34 of guidewire 16 out of the bore 20 of exchange catheter 18 through slit 22, to once again assume its configuration shown in FIGS. 1 and 2 in full lines. One can grasp proximal end 34 to prevent it from moving as exchange catheter 18 is withdrawn from the patient.

Exchange catheter 18 may be withdrawn in a series of steps of motion, in which the individual steps of withdrawal are on the order of one or two inches in length. After each step of withdrawal, which frequently causes guidewire 16 to move with the exchange catheter 18, one can once again advance guidewire 16 by sliding proximal section 34 forward in slit 22, to prevent guidewire 16 from being withdrawn too far so as to lose its advantageous position of extension through a stenosis or the like. By this means of stepwise withdrawal, exchange catheter 18 may be withdrawn without dislodging the guidewire from its desired position within the patient, to provide the desired and hitherto often impossible replacement of a guiding catheter or other catheter. The exchange catheter may also be removed by manually holding the exposed portion of guidewire 34 at a point close to the proximal end of guiding catheter 12 and slowly withdrawing exchange catheter 18 in a single movement.

Also, exchange catheter 18 may be formulated with a stiffness that assists in the advancement of guidewire 16, to facilitate the passage through difficult stenoses and the like.

The above has been offered for illustrative purposes only, and is not intended to limit the scope of the invention of this application, which is as defined in the claims below.

That which is claimed is:

1. The method of removing from a patient a first catheter which surrounds a guidewire, said first catheter and guidewire each having a distal portion emplaced in the cardiovascular system of a patient, which method comprises:

advancing into the patient to a desired position an exchange catheter, said exchange catheter surrounding said guidewire and being surrounded by said first catheter, while causing a proximal end portion of said guidewire to project outwardly through a longitudinal slit of said exchange catheter for grasping, to retain the guidewire in a desired position as the exchange catheter is advanced; and then placing said proximal end portion and any other guidewire portions that extend along said exchange catheter entirely within said exchange catheter, and withdrawing said first catheter from the patient, while causing the exchange catheter to be relatively stationary, whereby the guidewire within the exchange catheter is also retained in relatively stationary position without the need for retention of the guidewire by manual grasping.

2. The method of claim 1 in which said exchange catheter is of a length permitting grasping of the proximal end of the exchange catheter as the first catheter, surrounding the exchange catheter, is fully withdrawn from the patient.

3. The method of claim 1 in which the exchange catheter is advanced along the guidewire in guidewire-surrounding relation to a position in which the exchange catheter surrounds at least about ¾ of the length of the guidewire.

4. The method of claim 1 in which said first catheter is a guiding catheter for cardiovascular use.

5. The method of claim 1 in which said longitudinal slit is spaced from the catheter ends.

6. The method of claim 1 in which, after withdrawing said first catheter, a second catheter is threaded over the proximal end of said exchange catheter and advanced distally along the exchange catheter into the patient to a desired position.

7. The method of claim 6 in which the guidewire proximal end portion projecting out of the slit is thereafter grasped, and the exchange catheter is withdrawn from the patient.

8. The method of claim 7 in which said exchange catheter is withdrawn in steps of motion, and distally advancing the guidewire proximal end portion in said slit between said steps of motion.

9. The method of claim 1 in which the exchange catheter is unrolled from a spool as said exchange catheter is advanced into the patient.

10. A catheter system which comprises a first catheter implanted in a patient about a guidewire, and a flexible exchange catheter defining a catheter lumen extending through proximal and distal exchange catheter ends, said exchange catheter defining a longitudinal slit communicating between the lumen and the exterior of the exchange catheter, said exchange catheter being substantially coaxially positioned in a relation surrounding a major portion of said guidewire and being surrounded by said first catheter, to permit exchange of said first catheter without moving said guidewire, said exchange catheter being at least substantially twice the length of said first catheter.

11. The catheter system of claim 9 in which said guidewire defines a proximal end which projects laterally outwardly through said longitudinal slit at a position which is proximal of said first catheter.

12. The catheter system of claim 10 in which said guidewire defines a proximal end which projects laterally outwardly through said longitudinal slit at a position which is proximal of said first catheter.

13. The catheter system of claim 12 in which said longitudinal slit is spaced from the exchange catheter ends.

14. The catheter system of claim 10 in which said longitudinal slit is spaced from the exchange catheter ends.

15. The method of removing from a patient a first catheter which surrounds a guidewire without displacing the guidewire, said first catheter and guidewire each having a distal portion emplaced in the cardiovascular system of a patient, which method comprises:

advancing into the patient to a desired position an exchange catheter, said exchange catheter surrounding said guidewire and being surrounded by said first catheter, while causing a proximal end portion of said guidewire to project laterally outwardly through a longitudinal slit of said exchange catheter for grasping, to retain the guidewire in a desired position as the exchange catheter is advanced; and then placing the proximal end portion of the guidewire completely into said exchange catheter through said slit; withdrawing said first catheter from the patient while causing the exchange catheter to be relatively stationary, whereby the guidewire within the exchange catheter is also retained in relatively stationary position without the need for retention of the guidewire by manual grasping, said exchange catheter being of a length permitting grasping of the proximal end of the exchange catheter as the first catheter surrounding the exchange catheter is fully withdrawn from the patient; and, after withdrawing said first catheter, threading a second catheter over the proximal end of said exchange catheter, and advancing said second catheter distally in surrounding relation along the exchange catheter into the patient toward a desired position, while the proximal end portion of said guidewire is positioned within said exchange catheter.

16. The method of claim 15 in which the guidewire proximal end portion is thereafter moved to project out of the slit again and is grasped, and the exchange catheter is withdrawn from the patient.

17. The method of claim 16 in which the exchange catheter is advanced along the guidewire in guidewire-surrounding relation to a position in which the exchange catheter surrounds at least about three-quarters of the length of said guidewire.

18. The method of claim 17 in which the longitudinal slit of the exchange catheter is spaced from the catheter ends.

19. The method of claim 18 in which said first and second catheters are guiding catheters for cardiovascular use.

* * * * *